(12) United States Patent
Cegla et al.

(10) Patent No.: US 10,247,704 B2
(45) Date of Patent: Apr. 2, 2019

(54) ULTRASONIC DETECTION OF A CHANGE IN A SURFACE OF A WALL

(71) Applicant: PERMASENSE LIMITED, Horsham (GB)

(72) Inventors: Frederic Bert Cegla, Horsham (GB); Attila Gajdacsi, Horsham (GB)

(73) Assignee: PERMASENSE LIMITED, London (GB)

( * ) Notice: Subject to any disclaimer, the term of this patent is extended or adjusted under 35 U.S.C. 154(b) by 411 days.

(21) Appl. No.: 14/781,869

(22) PCT Filed: Mar. 26, 2014

(86) PCT No.: PCT/GB2014/050957
§ 371 (c)(1),
(2) Date: Oct. 1, 2015

(87) PCT Pub. No.: WO2014/167285
PCT Pub. Date: Oct. 16, 2014

(65) Prior Publication Data
US 2016/0033453 A1 Feb. 4, 2016

(30) Foreign Application Priority Data
Apr. 8, 2013 (GB) .................................. 1306304.5

(51) Int. Cl.
*G01N 29/44* (2006.01)
*G01N 29/04* (2006.01)
(Continued)

(52) U.S. Cl.
CPC ............. *G01N 29/04* (2013.01); *G01B 17/02* (2013.01); *G01B 17/06* (2013.01); *G01N 29/07* (2013.01);
(Continued)

(58) Field of Classification Search
CPC .... G01N 29/07; G01N 29/04; G01N 29/4409; G01N 29/348; G01N 29/44;
(Continued)

(56) References Cited

U.S. PATENT DOCUMENTS

| 3,554,013 | A | * | 1/1971 | Berg | ................... G01S 15/14 |
| | | | | | 73/609 |
| 3,918,296 | A | * | 11/1975 | Kitada | .................. G01S 7/529 |
| | | | | | 73/627 |

(Continued)

FOREIGN PATENT DOCUMENTS

| CN | 1654950 | 8/2005 |
| CN | 1784589 A | 6/2006 |

(Continued)

OTHER PUBLICATIONS

Canadian Office Action for Canadian application No. CA 2904772, Compeleted by the Canadian Patent Office, dated Sep. 29, 2016, 3 Pages.
(Continued)

*Primary Examiner* — Helen C Kwok
(74) *Attorney, Agent, or Firm* — Brooks Kushman P.C.

(57) ABSTRACT

A change in a surface of a wall is detected by transmitting a pulse of input ultrasonic vibrations into a proximal surface of the wall and then receiving ultrasonic vibrations from that proximal surface. The received ultrasonic vibrations are compared with a previously detected pulse of output ultrasonic vibrations that have been received from the proximal surface in order to identify, for example, a time of arrival of a current pulse of output ultrasonic vibrations. The time of arrival of this current pulse of output of ultrasonic vibrations may be used to detect a change in the surface of the wall, such as a change in the thickness of the wall. Other embodiments can detect a change in the roughness profile of the wall using changes in the received ultrasonic vibrations other than arrival time.

23 Claims, 7 Drawing Sheets

Figure 1:
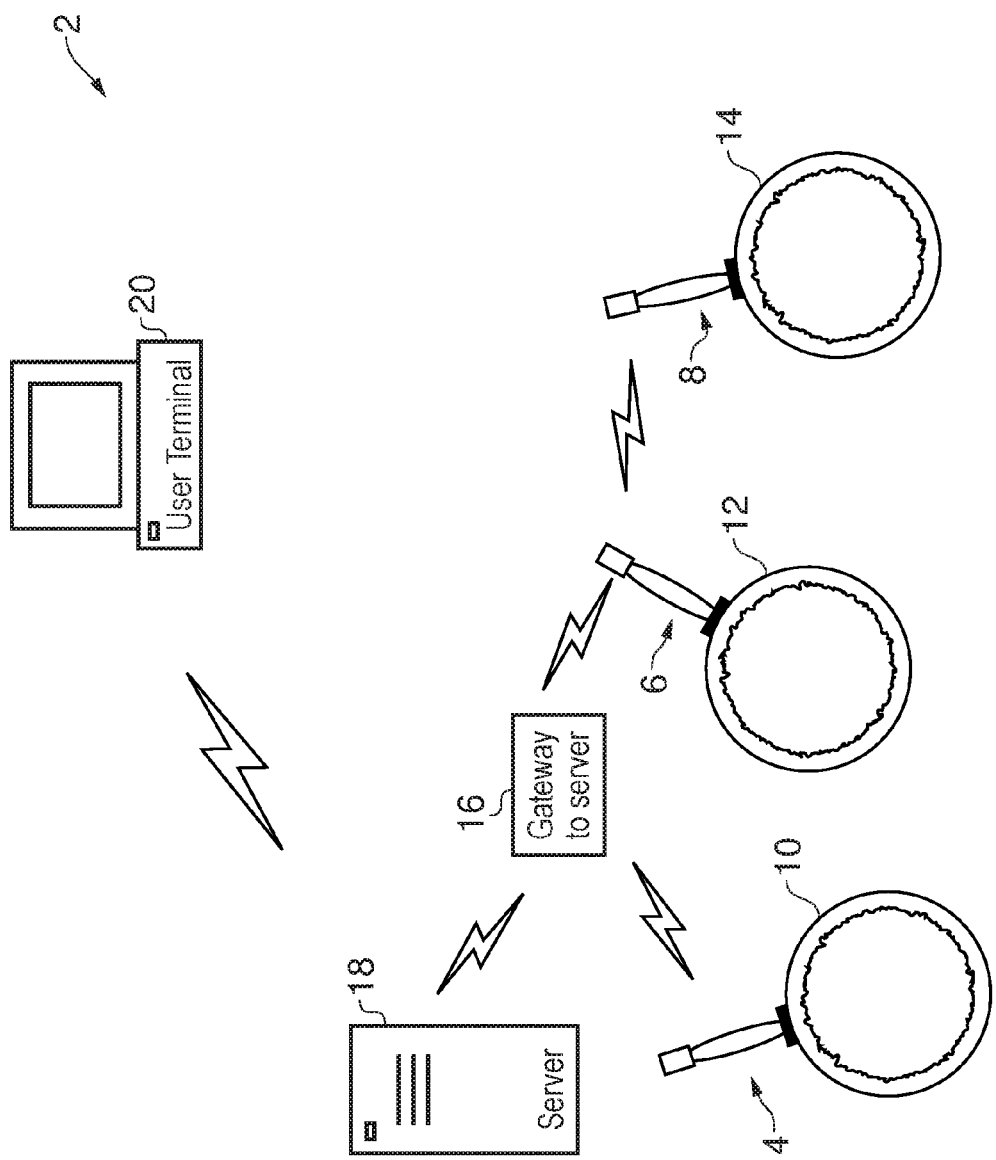

(51) Int. Cl.
G01B 17/02 (2006.01)
G01B 17/06 (2006.01)
G01N 29/07 (2006.01)

(52) U.S. Cl.
CPC ......... *G01N 29/44* (2013.01); *G01N 29/4409* (2013.01); *G01N 2291/02854* (2013.01); *G01N 2291/044* (2013.01)

(58) Field of Classification Search
CPC ............... G01N 29/343; G01N 29/265; G01N 29/4436; G01B 17/02; G01B 17/06; G01B 17/07
See application file for complete search history.

(56) References Cited

U.S. PATENT DOCUMENTS

| | | | | |
|---|---|---|---|---|
| 3,942,358 A * | 3/1976 | Pies | G01N 29/07 | 73/611 |
| 4,049,954 A * | 9/1977 | Da Costa Vieira | G01B 17/00 | 367/7 |
| 4,088,028 A * | 5/1978 | Hildebrandt | G01B 17/02 | 702/39 |
| 4,147,065 A * | 4/1979 | Lather | G01N 29/07 | 73/611 |
| 4,299,128 A * | 11/1981 | Gruber | G01N 29/07 | 73/627 |
| 4,324,141 A * | 4/1982 | Stearn | G01S 7/52004 | 367/108 |
| 4,388,830 A * | 6/1983 | Narushima | G01B 17/02 | 73/597 |
| 4,428,237 A * | 1/1984 | Zeger | G01N 29/48 | 73/592 |
| 4,432,235 A * | 2/1984 | Renzel | G01N 29/0627 | 327/58 |
| 4,435,984 A * | 3/1984 | Gruber | G01N 29/07 | 73/1.82 |
| 4,437,332 A * | 3/1984 | Pittaro | G01B 17/02 | 73/1.82 |
| 4,541,064 A * | 9/1985 | Livingston | G01N 29/449 | 702/36 |
| 4,545,248 A * | 10/1985 | Kitada | G01B 17/02 | 73/1.81 |
| 4,570,486 A * | 2/1986 | Volkmann | G01B 17/02 | 73/597 |
| 4,630,226 A * | 12/1986 | Tanaka | B60G 17/0165 | 367/127 |
| 4,658,649 A * | 4/1987 | Brook | G01N 29/0618 | 73/598 |
| 4,669,310 A * | 6/1987 | Lester | G01B 17/025 | 73/1.81 |
| 4,799,177 A * | 1/1989 | Sarr | G01B 7/02 | 702/171 |
| 4,881,409 A * | 11/1989 | Roarty | G01N 29/265 | 376/252 |
| 4,929,896 A * | 5/1990 | Lara | G01B 7/06 | 324/229 |
| 4,953,147 A * | 8/1990 | Cobb | E21B 47/082 | 181/105 |
| 5,009,103 A * | 4/1991 | Sato | G01B 17/02 | 702/171 |
| 5,060,518 A * | 10/1991 | Aleshin | G01N 29/07 | 73/620 |
| 5,072,388 A * | 12/1991 | O'Sullivan | E21B 47/082 | 181/105 |
| 5,176,034 A * | 1/1993 | Hazony | G01B 17/02 | 73/597 |
| 5,557,970 A * | 9/1996 | Abbate | G01B 17/02 | 702/170 |
| 5,952,577 A * | 9/1999 | Passi | G01N 29/069 | 600/445 |
| 5,965,818 A * | 10/1999 | Wang | G01B 17/02 | 73/598 |
| 6,035,717 A * | 3/2000 | Carodiskey | G01B 17/02 | 73/597 |
| 6,282,962 B1 | 9/2001 | Koch et al. | | |
| 6,571,634 B1 * | 6/2003 | Bazarov | G01N 29/265 | 73/623 |
| 6,584,847 B1 * | 7/2003 | Hirose | G01B 17/00 | 73/579 |
| 6,622,561 B2 * | 9/2003 | Lam | G01N 29/0609 | 73/620 |
| 7,495,455 B2 | 2/2009 | Sanoner et al. | | |
| 8,117,918 B2 * | 2/2012 | Gysling | G01B 17/02 | 73/623 |
| 8,156,784 B2 * | 4/2012 | DeAngelo | G01B 17/02 | 73/1.82 |
| 8,365,603 B2 * | 2/2013 | Lesage | G01N 29/0645 | 73/592 |
| 8,428,910 B2 * | 4/2013 | Papadimitriou | | 702/183 |
| 8,806,944 B2 * | 8/2014 | Grubb | G01N 29/043 | 73/597 |
| 2004/0250624 A1 * | 12/2004 | Abbate | G01B 17/02 | 73/597 |
| 2005/0186328 A1 | 8/2005 | Chatellier | | |
| 2007/0240512 A1 * | 10/2007 | Takada | G01N 29/041 | 73/588 |
| 2009/0139333 A1 * | 6/2009 | Hirose | G01N 29/069 | 73/579 |
| 2009/0143681 A1 * | 6/2009 | Jurvelin | A61B 8/0858 | 600/449 |
| 2010/0024556 A1 * | 2/2010 | Hirose | G01N 29/12 | 73/622 |
| 2010/0242613 A1 * | 9/2010 | Simard | G01N 29/262 | 73/641 |
| 2011/0162455 A1 * | 7/2011 | Renzel | G01N 29/343 | 73/632 |
| 2014/0020468 A1 * | 1/2014 | Smith | B06B 1/0207 | 73/597 |
| 2014/0148702 A1 * | 5/2014 | Chen | A61B 5/02007 | 600/454 |
| 2015/0053005 A1 * | 2/2015 | Smith | G01N 29/04 | 73/579 |
| 2015/0168243 A1 * | 6/2015 | Smith | G01L 11/06 | 73/703 |
| 2015/0330206 A1 * | 11/2015 | Trillon | G01N 17/04 | 138/103 |
| 2016/0202052 A1 * | 7/2016 | Smith | G01N 29/11 | 73/627 |

FOREIGN PATENT DOCUMENTS

| | | |
|---|---|---|
| CN | 101135554 A | 3/2008 |
| CN | 101806590 A | 8/2010 |
| CN | 102630302 A | 8/2012 |
| DE | 4414030 C1 | 8/1995 |
| DE | 19617455 | 11/1997 |
| GB | 2 128 330 A | 4/1984 |
| JP | 63145908 A | 6/1988 |
| JP | 03188390 A | 8/1991 |
| JP | H0682244 | 3/1994 |
| JP | H07198362 | 8/1995 |
| JP | 2000275035 A | 10/2000 |
| JP | 2004117137 | 4/2004 |
| JP | 2006078243 | 3/2006 |
| JP | 2010038710 | 2/2010 |
| JP | 2010164403 | 7/2010 |
| JP | 2011141236 | 7/2011 |

OTHER PUBLICATIONS

English Translation to Japanese Office Action to Japanese Application No. JP 2016505884, Completed by the Japanese Patent office, dated Oct. 18, 2016, 3 Pages.

Jarvis, A. J. C. et al., "Application of the distributed point source method to rough surface scattering and ultrasonic wall thickness measurement", J. Acoust. Soc. Am. 132, 2012, 12 pgs., Acoustical Society of America.

(56) References Cited

OTHER PUBLICATIONS

Chinese Office Action dated Mar. 1, 2017 for Chinese Application No. 201480019855.7, 5 pgs.
Jarvis, A. J. C. et al., "Application of the distributed point source method to rough surface scattering and ultrasonic wall thickness measurement," J. of the Acoustical Soc. of America 132 (3), Sep. 2012, pp. 1325-1335.
International Search Report dated Jun. 26, 2014 from PCT/GB2014/050957 filed Mar. 26, 2014, 11 pgs.
Search Report dated Apr. 28, 2013 from GB 1306304 published Feb. 7, 1973, 2 pgs.
New Zealand First Examination Report for IP No. 712010, dated Feb. 23, 2016, 4 Pages.

\* cited by examiner

Cross-Correlation (Sliding Dot Product)

▶ For continuous functions $\circ \ (f \otimes g)(t) \overset{\text{def}}{=} \int_{-\infty}^{\infty} f(\tau) g(t + \tau) d\tau$ ▶ For discrete functions $\circ \ (f \otimes g)[n] \overset{\text{def}}{=} \sum_{m=-\infty}^{\infty} (f(m) g(n + m))$ F() = previously detected pulse of output ultrasonic vibrations
g() = received ultrasonic vibrations

FIG. 7

ULTRASONIC DETECTION OF A CHANGE IN A SURFACE OF A WALL

CROSS-REFERENCE TO RELATED APPLICATION

This application is the U.S. national phase of PCT Application No. PCT/GB2014/050957 filed on Mar. 26, 2014, which claims priority to GB Patent Application No. 1306304.5 filed on Apr. 8, 2013, the disclosures of which are incorporated in their entirety by reference herein.

This invention relates to the field of ultrasonic testing. More particularly, this invention relates to the detection of a change in a surface of a wall.

It is known from WO-A-2007/051959 to provide ultrasonic detectors which may be used to perform non-destructive testing. One desirable type of testing is to detect a change in a surface of a wall. Such a wall may, for example, be the wall of a pipe containing a fluid, such as a corrosive fluid or a multi-phase fluid. Such fluids may corrode or erode the inner surface of the wall and it is desirable to monitor such changes in the thickness of the wall or changes in the roughness of the inner wall. By monitoring in this way, potential failures and risk can be identified before a problem arises. As an example, using monitoring techniques to track the corrosion or erosion of the inner surfaces of pipes in a refinery may permit the safe refining of oil which would otherwise be regarded as too difficult due to the way in which it corrodes or erodes the pipes of the refinery.

A problem with the above type of measurement is that the inner surface of the pipe may be corroded or eroded to form a rough surface which has the effect of scattering the ultrasonic vibrations being used to measure the wall thickness in a manner which results in unacceptable inaccuracy in the wall thickness measurements. A discussion of such rough surface scattering may be found in "Application Of The Distributed Point Source Method To Rough Surface Scattering And Ultrasonic Wall Thickness Measurement" by Jarvis and Cegla, Journal of the Acoustical Society of America 132(3), September 2012, pages 1325 to 1335.

Viewed from one aspect the present invention provides a method of detecting a change in a surface of a wall, said method comprising the steps of:

transmitting a pulse of input ultrasonic vibrations into a proximal surface of said wall, said pulse of input ultrasonic vibrations propagating through said wall to form a current pulse of output ultrasonic vibrations at said proximal surface;

receiving ultrasonic vibrations at said proximal surface;

comparing said received ultrasonic vibrations with a previously detected pulse of output ultrasonic vibrations received at said proximal surface to detect changes in said surface of said wall.

The present technique recognises that rough surface scattering can significantly alter the form of a detected pulse of ultrasonic vibrations (e.g. phase changes, waveform changes, dispersion etc) in a manner which makes it difficult accurately and reliably to detect the arrival time of a pulse of output ultrasonic vibrations being used to detect a change in a surface of a wall. A more accurate arrival time of a current pulse of output ultrasonic vibrations may be found by comparing the received ultrasonic vibrations with a previously detected pulse of output ultrasonic vibrations. The previously detected pulse of output ultrasonic vibrations will likely have a similar form as a current pulse of output ultrasonic vibrations to be detected and accordingly the comparison with this previously detected pulse of output ultrasonic vibrations may be used to more accurately identify the arrival time of the current pulse of output ultrasonic vibrations. Thus, received ultrasonic vibrations in which it is desired to identify a current pulse of output ultrasonic vibrations are compared with a historical detected pulse of ultrasonic vibrations which will likely have been subject to similar phase shifts, dispersions and waveform changes that rough surface scattering will impose.

In order to measure the thickness of the wall, the pulse of input ultrasonic vibrations propagates through the thickness of the wall, reflects from a distal surface of the wall and returns through the thickness of the wall to the proximal surface so as to form the current pulse of output ultrasonic vibrations. Thus, the proximal surface of the wall into which the pulse of input ultrasonic vibrations is sent may be the outer surface of a pipe and the distal surface may be the inner surface of a pipe which can be subject to corrosion or erosion resulting in rough surface scattering from that distal surface.

The input ultrasonic vibrations are produced at the proximal surface of the wall as this is accessible. The input ultrasonic vibrations may be directly applied to the proximal surface or may be applied via wedges, coupling fluids or other indirect mechanisms that will be familiar to those in this technical field. These various indirect ways of transmitting and receiving ultrasonic vibrations from the walls are all encompassed in the present techniques.

In some embodiments the pulse of input of ultrasonic vibrations may also propagate from an input location of the proximal surface in a direction substantially parallel to the proximal surface before being received at an output location of the proximal surface as a reference pulse of output ultrasonic vibrations that is received prior to the current pulse of ultrasonic vibrations at the output location. The direct propagation along the proximal surface of the wall generates a reference pulse which can be used to compensate for variations in the transmission and reception operations and so more accurately isolate a measurement relating to propagation of the ultrasonic vibrations through the thickness of the wall to a distal surface of the wall.

The comparison of the received ultrasonic vibrations with the previously detected pulse of ultrasonic vibrations may take a variety of different forms. The comparison could calculate cross-correlation values, cross-covariance values or similarity values using different time offsets and then use a maximum in these values to identify the time of arrival of the current pulse of ultrasonic vibrations. Correlating a current pulse of output ultrasonic vibrations with a previously detected pulse of output ultrasonic vibrations is more likely to accurately identify the time of arrival (time of maximum correlation) as the two pulses being compared will likely be subject to similar rough surface scattering influences.

The different time offsets for which the correlation values are determined as discussed above correspond to different propagation times of the ultrasonic vibrations through the wall being monitored. Such propagation delays may normally be a first-order propagation delay in which the ultrasonic waves traverse the wall once in each direction, but it is also possible that higher order propagation delays may be detected in which the ultrasonic waves traverse the wall more than once in each direction (although the increasing effects of rough surface scattering are likely to make such pulses increasingly difficult to accurately time).

It is possible that the comparison between the received ultrasonic signals and the previously detected pulse of output ultrasonic signals may be performed by directly comparing detected sample values for the vibrations concerned. However, it is also possible that this comparison could be performed in another domain, such as by Fourier transforming the vibrations or subjecting the vibrations to wavelet transformation before the comparison is made. Such variations in the signal processing associated with the comparison are all encompassed in the present techniques.

The change in the wall which is detected by the present techniques may be a change in the thickness of the wall as discussed above. It is also possible that the change in the wall may be a change in the surface profile of the wall which arises without any significant change in the overall thickness of the wall. Such changes in the profile of the wall may indicate, for example, the nature of any undesired processes occurring on a distal surface that is inaccessible as different processes may result in different changes to the profile of the distal surface.

The comparison may require storing a representation of a preceding pulse of output ultrasonic vibrations to serve as the previously detected pulse of output ultrasonic vibrations. This representation may be, for example, a sequence of sample values (possibly up-sampled) or may be a representation stored in another domain, such as the frequency domain or the domain associated with a wavelet transformation.

The representation may be direct in the sense of comprising a sequence of captured sample values from the previously detected pulse of output ultrasonic vibrations. In other embodiments the representation may be a modelled pulse of output ultrasonic vibrations which has been derived from a previously detected pulse of the ultrasonic vibrations (e.g. a previously detected pulse could be used to generate a model of the distal surface of a pipe and this model of the surface in turn used to model an output pulse of ultrasonic vibrations which can be compared with received ultrasonic vibrations from a subsequent pulse.

The preceding pulse of output ultrasonic vibrations used for the comparison may be an immediately preceding pulse of output ultrasonic vibrations as this is likely to have a highest correlation with a current pulse of output ultrasonic vibrations, but it is possible that previous pulses separated more greatly in time could be utilised with acceptable results.

When determining the thickness of the wall of a pipe, then the thickness measured may be used over time to monitor an internal corrosion rate of the pipe in a manner giving advance warning of potential failure of that pipe.

Viewed from another aspect the invention provides a method of signal processing to detect a change in a surface of a wall using a pulse of input ultrasonic vibrations transmitted into a proximal surface of said wall, said pulse of input ultrasonic vibrations propagating through said wall to form a current pulse of output ultrasonic vibrations at said proximal surface and ultrasonic vibrations received at said proximal surface, said method comprising the steps of:

comparing said received ultrasonic vibrations with a previously detected pulse of output ultrasonic vibrations received at said proximal surface to detect changes in said surface of said wall.

It will be appreciated that the transmission and reception of the ultrasonic vibrations may take place at a sensor location which is far removed from a location at which the comparison is performed which detects the time of arrival of a pulse of ultrasonic vibrations and the corresponding detection of, for example, the wall thickness. Sensors could perform the transmission and reception of ultrasonic vibrations and transmit the captured signals to a remote facility which then performs the comparison and detects the desired change in the wall before returning this result to the original site, or potentially a different site for interpretation and action by a user of the monitoring system.

Viewed from a further aspect the present invention provides a system for detecting a change in a surface of a wall, said system comprising:

a transmitter configured to transmit a pulse of input ultrasonic vibrations into a proximal surface of said wall, said pulse of input ultrasonic vibrations propagating through said wall to form a current pulse of output ultrasonic vibrations at said proximal surface;

a received configured to receive ultrasonic vibrations at said proximal surface;

processing circuitry configured to compare said received ultrasonic vibrations with a previously detected pulse of output ultrasonic vibrations received at said proximal surface to detect changes in said surface of said wall Viewed from a further aspect the present invention provides a signal processing apparatus for detecting a change in a surface of a wall using a pulse of input ultrasonic vibrations transmitted into a proximal surface of said wall, said pulse of input ultrasonic vibrations propagating through said wall to form a current pulse of output ultrasonic vibrations at said proximal surface and ultrasonic vibrations received at said proximal surface, said signal processing apparatus comprising:

processing circuitry configured to compare said received ultrasonic vibrations with a previously detected pulse of output ultrasonic vibrations received at said proximal surface to detect changes in said surface of said wall.

Figure 2:
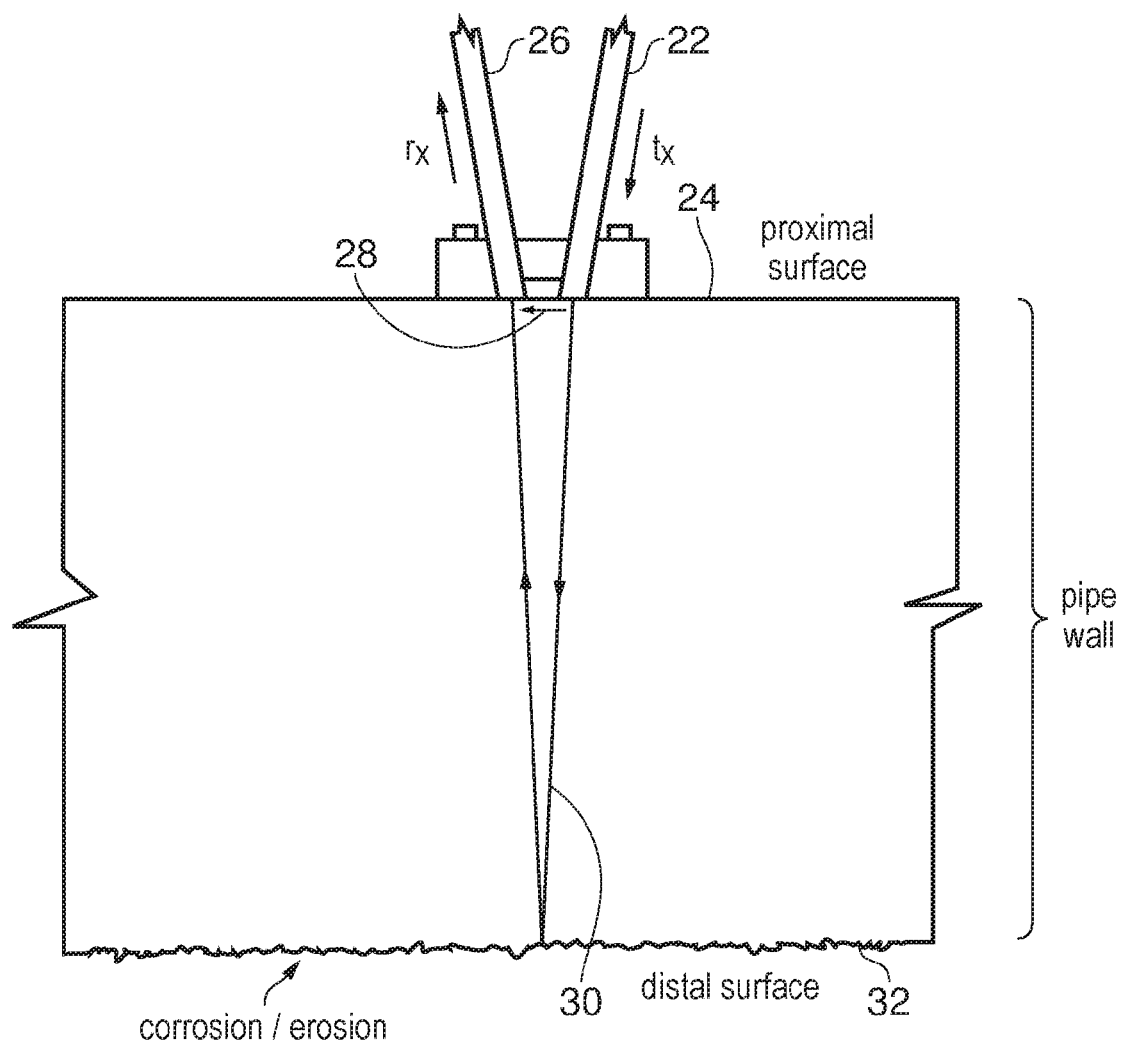
Figure 3:
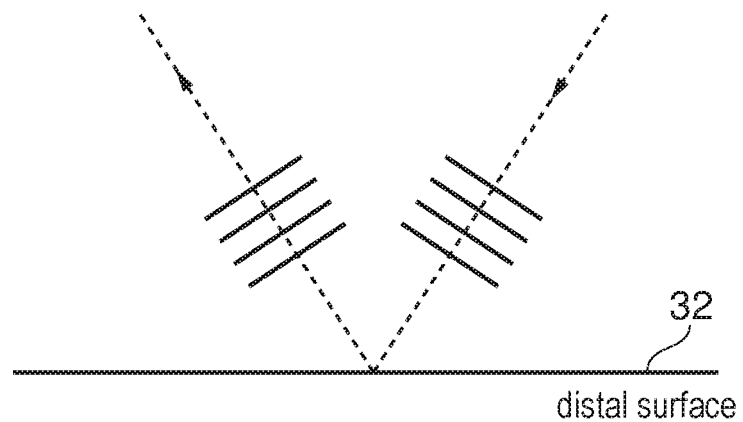
Figure 4:
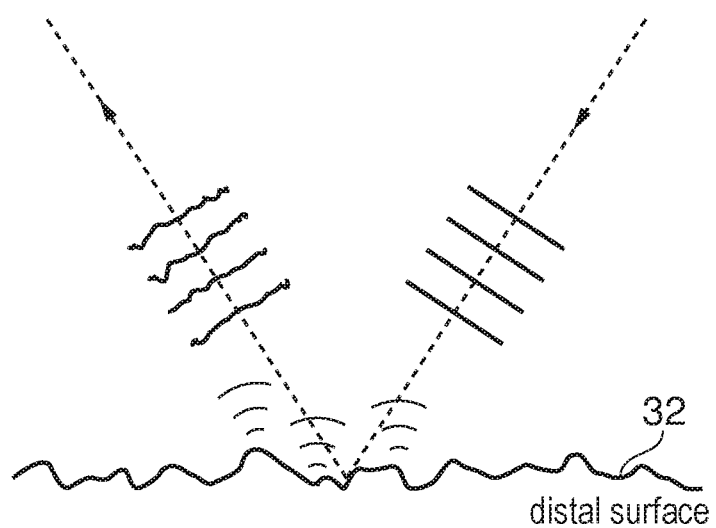
Figure 5:
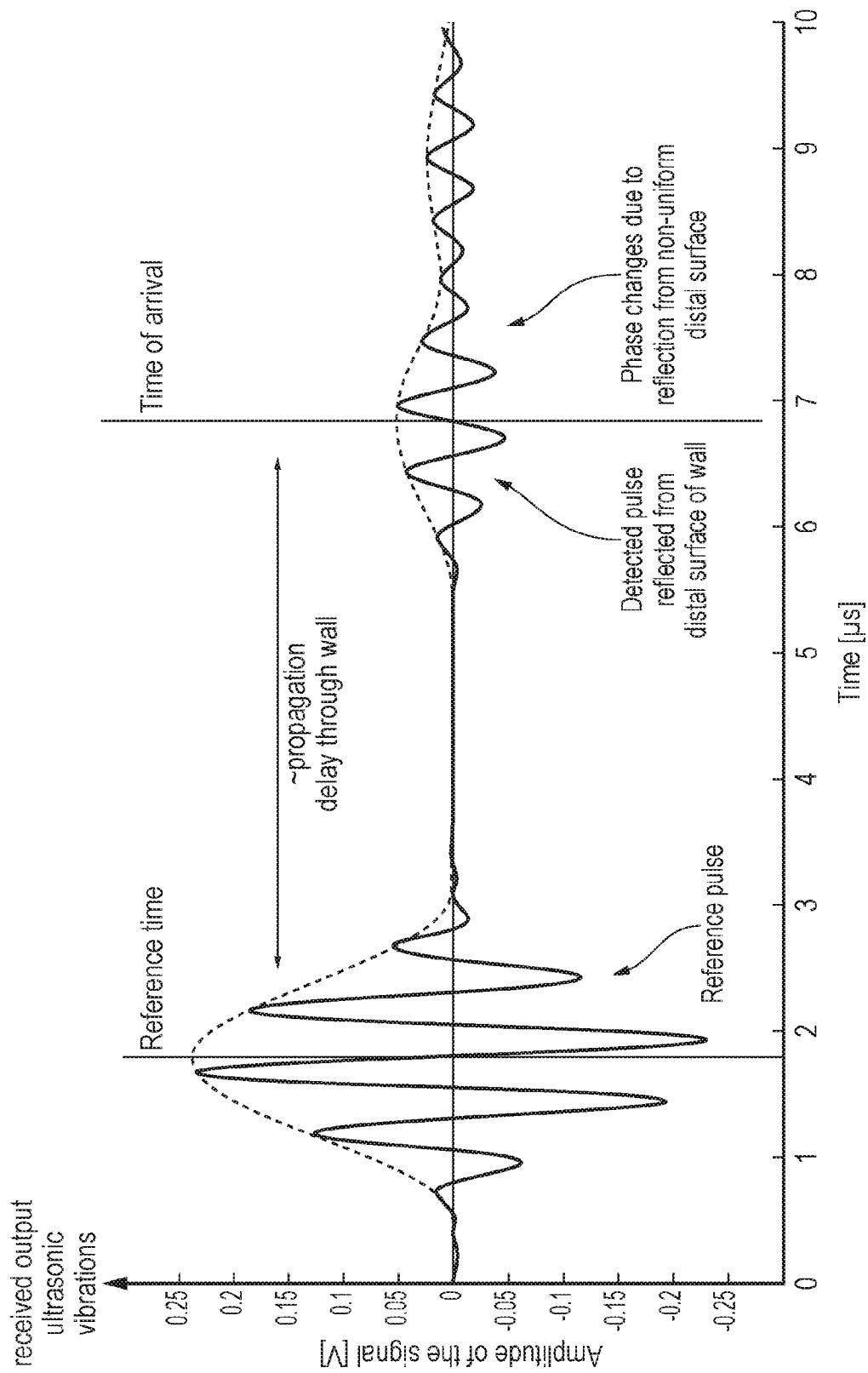
Figure 6:
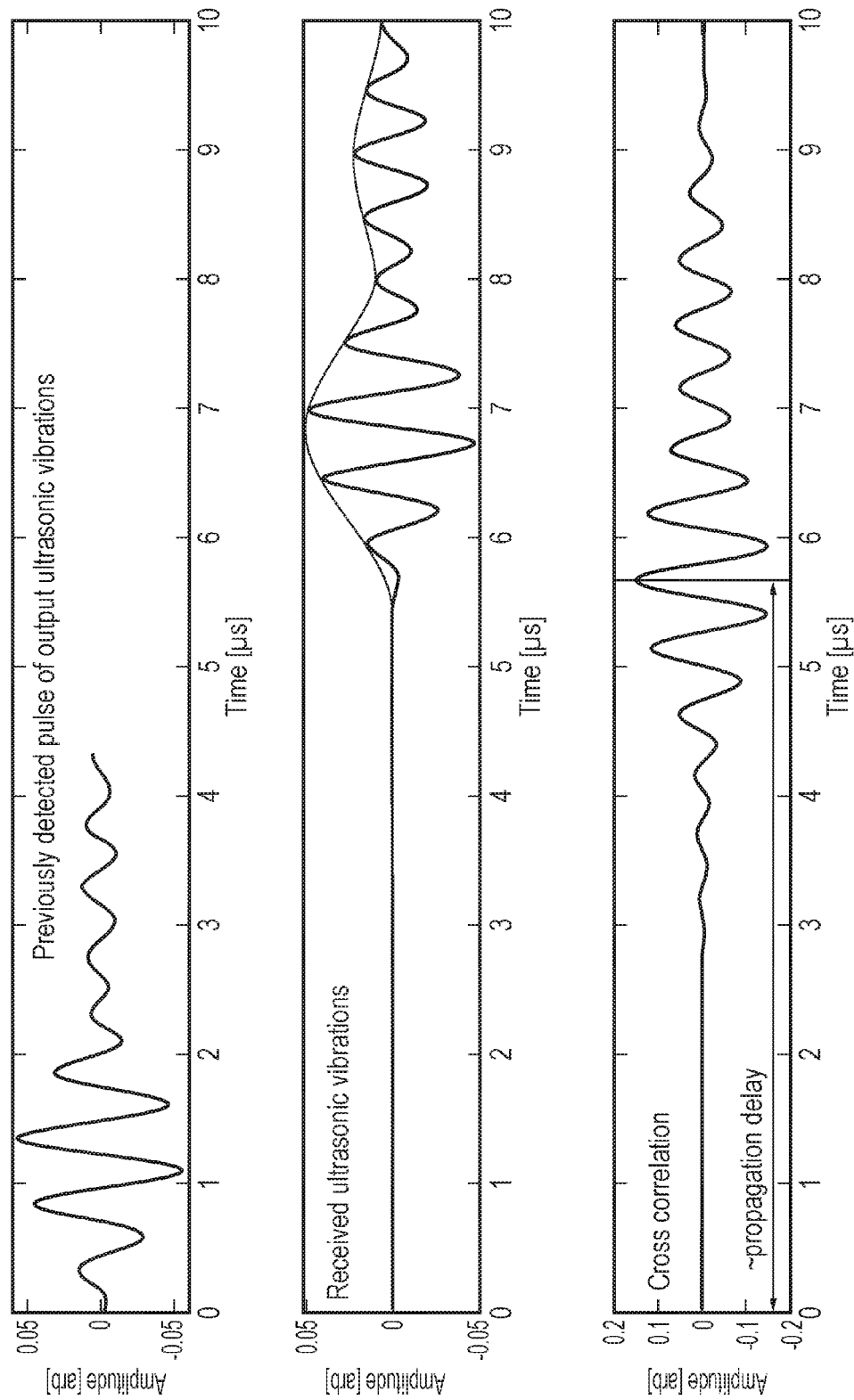
Figure 8:
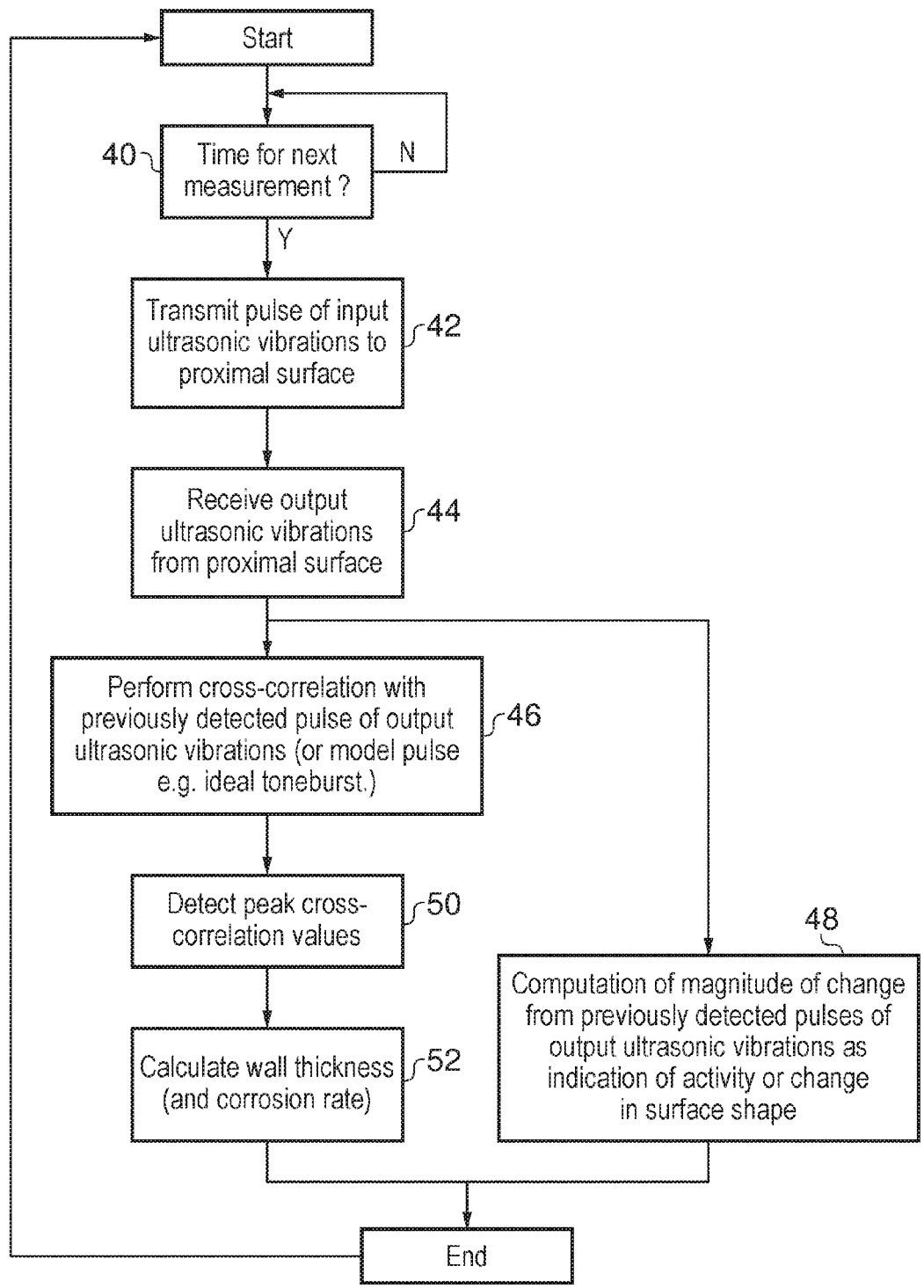

Embodiments of the invention will now be described, by way of example only, with reference to the accompanying drawings in which:

FIG. 1 schematically illustrates a system for monitoring pipe wall thickness;

FIG. 2 schematically illustrates the propagation of pulses of ultrasonic vibrations through a pipe wall;

FIG. 3 schematically illustrates the reflection of ultrasonic vibrations from a smooth surface;

FIG. 4 schematically illustrates the reflection of ultrasonic vibrations from a rough surface;

FIG. 5 schematically illustrates the receipt of a reference pulse and a detected pulse reflected from a distal surface of a wall;

FIG. 6 schematically illustrates the cross-correlation between a previously detected pulse of output ultrasonic vibrations and received ultrasonic vibrations;

FIG. 7 is a mathematical representation of the comparison step when performing cross-correlation (Sliding Dot Product); and FIG. 8 is a flow diagram schematically illustrating the use of ultrasonic vibrations and cross-correlation with a previously detected pulse to determine pipe wall thickness.

FIG. 1 schematically illustrates a system 2 for monitoring pipe wall thickness comprising a plurality of sensors 4, 6, 8 each attached to a respective pipe 10, 12, 14. Each pipe has an outer surface corresponding to a proximal surface to which one of the sensors 4, 6, 8, is attached and an inner surface corresponding to a distal surface from which reflections of pulses of ultrasonic vibrations are detected. The pipe may carry a corrosive fluid or a mixed phase fluid which subjects the inner surface of the pipe to corrosion and/or erosion (e.g. sand within crude oil may erode the inner surface of pipe). Each of the sensors 4, 6, 8 communicates wirelessly with a gateway 16 either directly or via a mesh network formed of the sensors. The gateway 16 in turn communicates with a server 18. The sensor 4, 6, 8 illustrated in FIG. 1 are waveguide sensors well suited to high temperature applications, but other sensor types are possible such as pulse echo mode sensors (same transducer sends and receives) that may be suited to lower temperature environments.

At periodic intervals, such as every 12 hours (or less if more frequent monitoring is required), each of the sensors 4, 6, 8 may perform a determination of the pipe wall thickness of the pipe 10, 12, 14 to which it is attached. This test may be performed by transmitting a pulse of input ultrasonic vibrations into a proximal surface of the pipe wall (either directly or indirectly via a wedge or coupling fluid) and then reflected ultrasonic vibrations returned back to the proximal surface. The received vibrations may be sampled with a high rate analogue-to-digital converter and then wirelessly transmitted via the gateway 16 to the server 18. The server 18 may then perform signal processing upon these signals representing the received ultrasonic vibrations at the proximal surface in order to identify a propagation delay of the ultrasonic pulses through the pipe walls and accordingly the pipe wall thicknesses. This signal processing uses a comparison of the received ultrasonic vibrations with a previously detected pulse of output ultrasonic vibrations that was received at the proximal surface in order to identify a time of arrival of a current pulse of output ultrasonic vibrations. This comparison may use cross-correlation, cross-covariance, a similarity function or other forms of comparison seeking to match received ultrasonic vibrations with a previously detected pulse of output ultrasonic vibrations. The analysis performed may determine the pipe wall thickness, but may also or alternatively be used to detect other changes in the distal (inner) surface of the pipe, such as changes in the inner surface profile of the pipe due to different types of corrosion/erosion.

The results of the analysis by the server 18 may be sent to a user terminal 20 where they can be displayed and interpreted by a user of the system. It will be appreciated that the pipes 10, 12, 14, the sensors 4, 6, 8 and the gateway 16 may be at a different physical location (such as in a completely different country) from the server 18 and in turn to the user terminal 20. The present techniques are well suited to remote monitoring of large scale plant, such as oil refineries or chemical processing plants.

FIG. 2 schematically illustrates the propagation of a pulse of ultrasonic vibrations through a pipe wall. The pulse of ultrasonic vibrations may be transmitted along a transmitting waveguide 22 to a proximal surface 24 of the pipe wall. The coupling to the proximal surface 24 may be direct or indirect. Received ultrasonic vibrations pass into a receiving waveguide 26 from the proximal surface 24 some time after the input pulse was sent into the pipe wall.

Illustrated in FIG. 2 is a direct path 28 between the transmitting waveguide 22 and the receiving waveguide 26. This direct path gives rise to a reference pulse of ultrasonic vibrations that may be used to compensate for the transmission times along the waveguides 22, 26 as well as other effects, such as delays in the triggering and transmission of the pulse. (other transducers operating in a pulse echo mode may use reflection from the proximal surface as the timing trigger). A first-order reflecting path 30 through the wall is illustrated showing the input ultrasonic vibrations propagating through the thickness of the wall, reflecting from a distal surface 32 of the wall and then returning through the thickness of the wall back to the proximal surface 24 where they form the current pulse of output ultrasonic vibrations for which the arrival time is detected using the cross-correlation, cross-co-variance, similarity functions or other forms of comparison as previously discussed. Determining the arrival time of this current pulse of output ultrasonic vibrations relative to the arrival time of the reference pulse permits a propagation delay time to be calculated corresponding to the propagation through the thickness of the pipe wall using standard trigonometry. This propagation delay may in return be used to determine a wall thickness and monitor factors such as the rate of corrosion or the rate of erosion of the wall.

FIG. 3 schematically illustrates the reflection of a pulse of ultrasonic vibrations from a smooth distal surface 32. In this case, as the distal surface 32 is smooth (at least at a scale relative to the wavelength of the ultrasonic vibrations), then the reflection will be uniform and the reflected ultrasonic waves will suffer no unpredictable changes in phase, undesirable dispersion or other changes in their waveform.

FIG. 4 schematically illustrates the reflection of a pulse of ultrasonic vibrations from a rough distal surface 32. The rough distal surface 32 gives rise to rough surface scattering in which reflections from the peaks and troughs in the roughened surface interfere with each other and produce a reflected pulse of ultrasonic vibrations which are subject to changes in phase, dispersion and other changes in its waveform that vary considerably with the backwall shape. These changes in the waveform of the reflected pulse of ultrasonic vibrations that result from unpredictable changes in backwall shape make it difficult to accurately identify a time of arrival of that reflected pulse of ultrasonic vibrations.

FIG. 5 schematically illustrates received output ultrasonic vibrations at a proximal surface. A short time after the pulse of input ultrasonic vibrations is transmitted into the wall, a reference pulse of ultrasonic vibrations will be received corresponding to propagation of those ultrasonic vibrations parallel to the surface of the wall. At a later time the detected pulse reflected from the distal surface of the wall is received. The first-order reflected pulse will be the first to be received. In practice, the second-order and higher-order pulses may be too dispersed/confused to be accurately detected when the backwall is not smooth, but for smooth backwalls may provide useful additional information. FIG. 5 schematically illustrates that the detected pulse reflected from the distal surface of the wall has been subject to phase changes and dispersion due to reflection from the non-uniform distal surface in a manner which lengthens the pulse in time and changes the detailed phasing of the signal. The result of these distortions introduced by reflection from the non-uniform distal surface is that a correlation of the detected pulse with an input pulse or a model of the input pulse would produce an unreliable time of arrival.

FIG. 6 schematically illustrates how the received ultrasonic vibrations from the detected pulse reflected from the distal surface wall may be compared with a previously detected pulse of output ultrasonic vibrations using a technique such as cross-correlation to determine the arrival time of the current pulse of output ultrasonic vibrations in the received ultrasonic vibrations. As the previously detected pulse of ultrasonic vibrations will likely have been subject to similar distortions as the current pulse of output ultrasonic vibrations (as the changes in the roughness of the distal wall are relatively slow), then a more accurate result may be achieved from the cross-correlation comparison and a more accurate arrival time determined. This arrival time approximately corresponds to the propagation delay of the pulse through the pipe wall and accordingly may be used to determine the wall thickness and factors such as the rate of changeable thickness due to corrosion/erosion.

The previously detected pulse of output ultrasonic vibrations illustrated at the top of FIG. 6 may be stored as a sequence of sample values within the server 18 from the immediately preceding detected pulse. The comparison illustrated in FIG. 6 is a direct comparison of sampled values varying with time. The comparison could also be performed in a different domain, such as transforming both the received ultrasonic vibrations and the previously detected pulse using a wavelet transformation and then performing the comparison in that different domain or by transforming to the frequency domain and performing the comparison in that different domain. Another alternative is that instead of performing the comparison directly against the previously detected pulse of output ultrasonic vibrations or a transformed version of that pulse, it is also possible that in comparison may be performed against a model pulse which has been derived from the previously detected pulse of output of ultrasonic vibrations. This model pulse can be intended to model the variations in the waveform which are being produced by the current state of roughness of the distal wall from which the reflection is being made. In the case of roughness determination the comparison between successive signals may be indirect, e.g. compare successive signals with some simple shape and monitor changes in the comparison measure. These alternatives are all encompassed within the present technique.

FIG. 7 schematically illustrates a mathematical function for performing cross-correlation (sliding dot product) as one example form of comparison in order to identify the time of arrival. This cross-correlation is represented both for continuous functions and for discrete functions. In practice the signal processing is most likely to be performed in relation to the discrete function variant as the sample values of the received ultrasonic vibrations will be discrete values.

FIG. 8 is a flow diagram schematically illustrating the measurement of wall thickness in accordance with one example embodiment of the present technique. At step 40 processing waits until it is time for the next measurement to be made. Such measurements may be made periodically, such as daily or twice daily. At step 42 a pulse of input ultrasonic vibrations is transmitted into the proximal surface of the wall. Step 44 then receives the output ultrasonic vibrations from the proximal surface of the wall. The received ultrasonic vibrations may be transmitted to the remote server 18. It is also possible that in some embodiments all the signal processing could be performed at the sensor 4, 6, 8 itself so as to reduce the amount of data transmission required (e.g. in undersea applications).

At step 46 cross-correlation is performed between the received ultrasonic vibrations and a previously detected pulse of output ultrasonic vibrations using different time offsets (as is inherent in determining a cross-correlation) sometimes the previously detected pulse of output ultrasonic vibrations may be replaced by a modelled representation or, particularly when processing the first signal captured when there is no previous captured pulse, by an ideal toneburst. The time offset which produces the largest value for this cross-correlation corresponds to the best match between the received ultrasonic vibrations and the previously detected pulse and accordingly corresponds to the time of arrival of the current pulse of ultrasonic vibrations. A model pulse may be fitted to the received ultrasonic vibrations before the comparison is made in some embodiments. The received and previously detected vibrations may also be up-sampled prior to the comparison step. The peak in the cross-correlation value is detected at step 50 and is then used at step 52 to determine the wall thickness (using trigonometry and the known speed of the ultrasonic vibrations through the wall material at the temperature concerned (temperature compensation may be used)). The wall thickness in turn may be used to derive data such as a corrosion or erosion rate of the wall. This result data may be transmitted to the user terminal 20 for interpretation and action by a user.

As an alternative or addition to the determination of wall thickness, the received ultrasonic vibrations can be used at step 48 to detect changes in the backwall other than thickness changes, e.g. changes in backwall roughness indicative of unwanted changes in the backwall. Such changes may not change the arrival time of the reflected pulse significantly, but other changes (e.g. phase, shape, dispersion) can be used to determine a change in surface roughness of the backwall.

The very first measured signal cannot be cross-correlated with a previously measured signal as there is none. In this case an ideal tone burst may be used as the reference. The ideal tone burst may be generated with the same parameters as the tone burst used as the sent signal, but may have different phase values—the precise signal is not critical to such an initialisation. In the case of a very rough backwall surface, this comparison with an ideal tone burst may result in a large offset error because the time or arrival could not be reliably determined. However, the thickness loss (corrosion rate) can still be reliably tracked.

The invention claimed is:

1. A method of detecting a change in a surface of a wall, said method comprising the steps of:
transmitting a pulse of input ultrasonic vibrations into a proximal surface of said wall, said pulse of input ultrasonic vibrations propagating through said wall and reflecting from a distal surface of said wall to form a reflected pulse of output ultrasonic vibrations at said proximal surface;
receiving said reflected pulse of output ultrasonic vibrations at said proximal surface; and
comparing said received reflected pulse of output ultrasonic vibrations with a previously detected pulse of output ultrasonic vibrations reflected from said distal surface of said wall and received at said proximal surface to detect changes in said surface of said wall, wherein said received reflected pulse of output ultrasonic vibrations and said previously detected pulse of output ultrasonic vibrations comprise vibrations reflected from said distal surface of said wall in response to different pulses of input ultrasonic vibrations; and
a time of arrival of said received reflected pulse of output ultrasonic vibrations is determined based on a comparison between said received reflected pulse of output ultrasonic vibrations and said previously detected pulse of output ultrasonic vibrations.

2. The method as claimed in claim 1, wherein said pulse of input ultrasonic vibrations propagates from an input location of said proximal surface in a direction substantially parallel to said proximal surface before being received at an output location of said proximal surface as a reference pulse of output ultrasonic vibrations prior to receipt of said reflected pulse of output ultrasonic vibrations at said output location.

3. The method as claimed in claim 1, wherein said step of comparing:
(i) calculates cross-correlation values between said previously detected pulse of output ultrasonic vibrations and said received reflected pulse of output ultrasonic vibrations; and (ii) identifies a maximum in said cross-correlations values as corresponding to a time of arrival of said reflected pulse of output ultrasonic vibrations.

4. The method as claimed in claim 1, wherein said step of comparing:
   (i) calculates cross-covariance values between said previously detected pulse of output ultrasonic vibrations and said received reflected pulse of output ultrasonic vibrations; and
   (ii) identifies a maximum in said cross-covariance values as corresponding to a time of arrival of said reflected pulse of output ultrasonic vibrations.

5. The method as claimed in claim 1, wherein said step of comparing:
   (i) calculates similarity values between said previously detected pulse of output ultrasonic vibrations and said received reflected pulse of output ultrasonic vibrations; and
   (ii) identifies a maximum in said similarity values as corresponding to a time of arrival of said reflected pulse of output ultrasonic vibrations.

6. The method as claimed in claim 1, wherein said previously detected pulse of output ultrasonic vibrations and said received reflected pulse of output ultrasonic vibrations are transformed to one of a frequency domain and a wavelet domain prior to said step of comparing.

7. The method as claimed in claim 1, wherein said change in said surface corresponds to a change in thickness of said wall.

8. The method as claimed in claim 1, wherein said change in said surface corresponds to a change in profile of said surface of said wall.

9. The method as claimed in claim 1, comprising storing a representation of a preceding pulse of output ultrasonic vibrations to serve as said previously detected pulse of output ultrasonic vibrations.

10. The method as claimed in claim 9, wherein said representation is one of:
    a sequence of sample values captured from said previously detected pulse of output ultrasonic vibrations; and
    a modelled pulse of output ultrasonic vibrations derived from said previously detected pulse of output ultrasonic vibrations.

11. The method as claimed in claim 9, wherein said preceding pulse of output ultrasonic vibrations is an immediately preceding pulse of output ultrasonic vibrations.

12. The method as claimed in claim 1, wherein said received reflected pulse of output ultrasonic vibrations and said previously detected pulse of output ultrasonic vibrations are up-sampled prior to said comparing.

13. The method as claimed in claim 1, wherein a model pulse is fitted to said received reflected pulse of output ultrasonic vibrations and then compared with said previously detected pulse of output ultrasonic vibrations.

14. The method as claimed in claim 1, wherein said wall has at least one non-uniform surface.

15. The method as claimed in claim 1, wherein said wall forms a pipe.

16. The method as claimed in claim 14, wherein said wall is subject to corrosion resulting in said non-uniform surface.

17. The method as claimed in claim 15, wherein said pipe carries a corrosive fluid and said detecting of said change is used to monitor internal corrosion of said pipe.

18. The method as claimed in claim 17, comprising determining a rate of change of thickness of said wall to monitor an internal corrosion rate of said pipe.

19. The method as claimed in claim 14, wherein said wall is subject to erosion resulting in said non-uniform surface.

20. The method as claimed in claim 15, wherein said pipe carries a multiphase fluid and said detecting of said change is used to monitor internal erosion of said pipe.

21. A method of signal processing to detect a change in a surface of a wall using a pulse of input ultrasonic vibrations transmitted into a proximal surface of said wall, said pulse of input ultrasonic vibrations propagating through said wall and reflecting from a distal surface of said wall to form a reflected pulse of output ultrasonic vibrations at said proximal surface, said method comprising the steps of:
   comparing said reflected pulse of output ultrasonic vibrations with a previously detected pulse of output ultrasonic vibrations reflected from said distal surface of said wall and received at said proximal surface to detect changes in said surface of said wall, wherein said reflected pulse of output ultrasonic vibrations and said previously detected pulse of output ultrasonic vibrations comprise vibrations reflected from said distal surface of said wall in response to different pulses of input ultrasonic vibrations; and
   a time of arrival of said reflected pulse of output ultrasonic vibrations is determined based on a comparison between the reflected pulse of output ultrasonic vibrations and the previously detected pulse of output ultrasonic vibrations.

22. A system for detecting a change in a surface of a wall, said system comprising:
   a transmitter configured to transmit a pulse of input ultrasonic vibrations into a proximal surface of said wall, said pulse of input ultrasonic vibrations propagating through said wall and reflecting from a distal surface of a wall to form a reflected pulse of output ultrasonic vibrations at said proximal surface;
   a receiver configured to receive said reflected pulse of output ultrasonic vibrations at said proximal surface;
   processing circuitry configured to compare said received reflected pulse of output ultrasonic vibrations with a previously detected pulse of output ultrasonic vibrations reflected from said distal surface of said wall and received at said proximal surface to detect changes in said surface of said wall, wherein said received reflected pulse of output ultrasonic vibrations and said previously detected pulse of output ultrasonic vibrations comprise vibrations reflected from said distal surface of said wall in response to different pulses of input ultrasonic vibrations; and
   said processing circuitry is configured to determine a time of arrival of said received reflected pulse of output ultrasonic vibrations based on a comparison between the received reflected pulse of output ultrasonic vibrations and the previously detected pulse of output ultrasonic vibrations.

23. A signal processing apparatus for detecting a change in a surface of a wall using a pulse of input ultrasonic vibrations transmitted into a proximal surface of said wall, said pulse of input ultrasonic vibrations propagating through said wall and reflecting from a distal surface of said wall to form a reflected pulse of output ultrasonic vibrations at said proximal surface, said signal processing apparatus comprising:
   processing circuitry configured to compare said reflected pulse of output ultrasonic vibrations with a previously detected pulse of output ultrasonic vibrations reflected from said distal surface of said wall and received at said proximal surface to detect changes in said surface of said wall, wherein said reflected pulse of output ultrasonic vibrations and said previously detected pulse of output ultrasonic vibrations comprise vibrations reflected from said distal surface of said wall in response to different pulses of input ultrasonic vibrations; and said processing circuitry is configured to determine a time of arrival of said reflected pulse of output ultrasonic vibrations based on a comparison between the reflected pulse of output ultrasonic vibrations and the previously detected pulse of output ultrasonic vibrations.

\* \* \* \* \*